United States Patent [19]
Boyd et al.

[11] Patent Number: 5,916,522
[45] Date of Patent: Jun. 29, 1999

[54] ELECTROCHEMICAL ANALYTICAL CARTRIDGE

[75] Inventors: Douglas E. Boyd, Dublin; Jan B. Yates, Reynoldsburg; Ronald K. Coleman, Columbus, all of Ohio

[73] Assignee: Careside, Inc., Culver City, Calif.

[21] Appl. No.: 09/079,034

[22] Filed: May 14, 1998

Related U.S. Application Data

[63] Continuation-in-part of application No. 08/907,426, Aug. 7, 1997, and application No. 09/014,558, Jan. 28, 1998.

[51] Int. Cl.⁶ .............................. G01N 1/38; G01N 21/07
[52] U.S. Cl. ................................ 422/58; 422/72; 422/81; 422/100; 422/101; 422/102; 422/103; 436/45; 436/174; 436/177; 436/179; 436/180
[58] Field of Search ........................... 422/58, 61, 72, 422/81, 100, 101, 102, 82.03, 103; 436/43, 45, 164, 165, 174, 177, 179, 180

[56] References Cited

U.S. PATENT DOCUMENTS

| | | | |
|---|---|---|---|
| 4,708,940 | 11/1987 | Yoshida et al. | 436/45 |
| 4,740,472 | 4/1988 | Burtis et al. | 436/63 |
| 4,788,154 | 11/1988 | Guigan | 436/180 |
| 4,814,144 | 3/1989 | Edelmann et al. | 422/102 |
| 4,883,763 | 11/1989 | Holen et al. | 436/45 |
| 4,940,527 | 7/1990 | Kazlauskas et al. | 204/401 |
| 4,963,498 | 10/1990 | Hillman et al. | 436/69 |
| 5,061,381 | 10/1991 | Burd | 210/789 |
| 5,096,669 | 3/1992 | Lauks et al. | 422/61 |
| 5,122,284 | 6/1992 | Braynin et al. | 210/782 |
| 5,147,607 | 9/1992 | Mochida | 422/57 |
| 5,160,702 | 11/1992 | Kopf-Sill et al. | 422/72 |
| 5,171,533 | 12/1992 | Fine et al. | 422/72 |
| 5,186,844 | 2/1993 | Burd et al. | 210/782 |
| 5,242,606 | 9/1993 | Braynin et al. | 210/787 |
| 5,275,016 | 1/1994 | Chatterjee et al. | 62/381 |
| 5,286,454 | 2/1994 | Nilsson et al. | 422/102 |
| 5,288,463 | 2/1994 | Chemelli | 422/58 |
| 5,304,348 | 4/1994 | Burd et al. | 422/72 |
| 5,399,486 | 3/1995 | Cathey et al. | 435/7.9 |
| 5,403,415 | 4/1995 | Schembri | 156/73.1 |
| 5,409,665 | 4/1995 | Burd | 422/64 |
| 5,413,732 | 5/1995 | Buhl et al. | 252/182.11 |
| 5,416,026 | 5/1995 | Davis | 436/66 |
| 5,427,915 | 6/1995 | Ribi et al. | 435/7.92 |
| 5,447,440 | 9/1995 | Davis et al. | 435/6 |

(List continued on next page.)

FOREIGN PATENT DOCUMENTS

| | | |
|---|---|---|
| 0 160 282 B1 | 1/1990 | European Pat. Off. . |
| 0 397 424 A2 | 11/1990 | European Pat. Off. . |
| 0 407 827 A2 | 1/1991 | European Pat. Off. . |
| 0 430 248 A2 | 6/1991 | European Pat. Off. . |
| 0 318 255 B1 | 4/1993 | European Pat. Off. . |
| 0 381 501 B1 | 6/1994 | European Pat. Off. . |
| 0 470 202 B1 | 6/1994 | European Pat. Off. . |
| 0 482 721 B1 | 9/1995 | European Pat. Off. . |
| 0 550 090 B1 | 9/1996 | European Pat. Off. . |
| 82 06036 | 4/1982 | France . |
| WO 90/13016 | 11/1990 | WIPO . |
| WO/96/06354 | 2/1996 | WIPO . |

*Primary Examiner*—Long V. Le
*Attorney, Agent, or Firm*—Oppenheimer Wolff & Donnelly LLP

[57] ABSTRACT

An electro-analytical cartridge adapted for use in analyzing fluids. The cartridge includes an electrochemical device that measures ionic activity using ion-specific electrodes. The cartridge further includes a plumbing system composed of the electrochemical device and various wells or chambers which are interconnected by passageways. After introduction into the cartridge, liquid samples are measured out and transported to the electrochemical device utilizing a sequential application of centrifugal force followed by pressurization of the system. Reference fluid is transported from a reference fluid well or reservoir to the electrochemical device for use in measuring ionic activity. The cartridge may be used to measure the ionic activity of a wide variety of ions in fluids including bodily fluids.

17 Claims, 6 Drawing Sheets

U.S. PATENT DOCUMENTS

| | | | |
|---|---|---|---|
| 5,449,621 | 9/1995 | Klein | 436/45 |
| 5,457,053 | 10/1995 | Burd et al. | 436/45 |
| 5,472,063 | 12/1995 | Schembri | 210/380.1 |
| 5,472,671 | 12/1995 | Nilsson et al. | 422/102 |
| 5,478,750 | 12/1995 | Bernstein et al. | 436/164 |
| 5,500,187 | 3/1996 | Deoms et al. | 422/58 |
| 5,503,985 | 4/1996 | Cathey et al. | 435/7.9 |
| 5,589,399 | 12/1996 | Allen et al. | 436/169 |

ELECTROCHEMICAL ANALYTICAL CARTRIDGE

This application is a continuation-in-part of copending U.S. patent application Ser. Nos. 08/907,426, and 09/014,558, which were filed on Aug. 7, 1997 and Jan. 28, 1998, respectively.

BACKGROUND OF THE INVENTION

1. Field of the Invention

The present invention relates generally to systems and methods which are used in electrochemical analysis. More particularly, the present invention relates to electrochemical instruments and methods which are used to analyze the ionic activity fluids in a wide variety of laboratories including clinical laboratories and other healthcare facilities.

2. Description of the Related Art

Clinical chemistry involves the qualitative and quantitative analyses of body fluids, such as blood, urine, spinal fluid and other materials. Clinical chemistry encompasses multiple specialty testing areas including coagulation, hematology, immunochemistry, as well as chemistry. The test results derived from such analyses are used by physicians and other healthcare professionals to diagnose, monitor and treat diseases. The analysis protocols, instrumentation and other equipment utilized in clinical laboratory testing must be capable of providing accurate and repeatable test results. In addition, it is desirable that the procedures and instrumentation be simple and efficient. The testing equipment and procedures should be versatile enough that they can be used in healthcare locations where relatively few samples are tested as well as in larger clinical laboratories where the number of samples being tested on a daily basis is quite large.

A wide variety of analysis protocols are based on electrochemical analysis of the fluid being tested or the reaction product(s) of the fluid and one or more reagents. The majority of electrochemical procedures which apply to clinical chemistry involve potentiometry, polarography, amperometry, coulometry, and conductometry. Potentiometry is one of the more widely used electrochemical analytical techniques. In potentiometry, the electrode potential difference between two electrodes in an electrochemical cell is measured. Many procedures involve measuring the change in electric potential over a period of time. In addition, a wide variety of ion-specific electrodes, as well as specialized electrolyte solutions, have been developed. Electrochemistry procedures are available for measuring a wide variety of ions present in biological fluids, including sodium, potassium, chloride, fluoride, and calcium ions.

Major consideration in designing analytical equipment for use by healthcare personnel is the amount of sample available for testing. In many situations, the amount of blood or other bodily fluid available is relatively small. Accordingly, there has been a trend in clinical chemistry to develop analytical systems which are capable of conducting numerous different chemical analyses on relatively small amounts of sample. In general, the goal has been to develop clinical analytical systems which provide the maximum number of medical tests utilizing the minimum amount of sample.

In achieving the above goals, a multitude of different analytical procedures and approaches have been investigated. In one approach, instruments have been developed which have a single sample introduction site. The equipment is designed so that the sample is split and routed to various locations within the system where multiple chemical analyses take place. Other systems do not include internal sample splitting devices and rely on the clinical chemist to separate the sample into small aliquots which are introduced into various instruments which are capable of conducting a maximum of only a few chemical analyses at one time.

In the field of clinical electrochemistry, a number of devices have been developed for determining the ionic activity in relatively small amounts of fluid (i.e. 10–50 $\mu$l). Such devices generally include a plurality of ion-selective solid electrode pairs which are associated with liquid distribution porous membranes and a porous capillary bridge which are oriented to provide electrical conduction between the two electrodes when the test solution and reference solution are spotted onto the porous members. The electrodes and porous members are housed in a support frame which includes covers having apertures through which liquid is introduced into the device. These multiple electrode devices are used to simultaneously determine ionic activity of different ions in test solutions such as whole blood, plasma, serum and urine. These types of devices are disclosed in U.S. Pat. Nos. 4,437,970; 4,865,698; 4,528,085; 4,510,035; 4,655,899; 5,626,740; 4,555,274; 4,571,293; 4,615,788; 4,684,445; 4,871,441; and 5,021,140. These patents are all assigned to Fuji Photo Film Company, and the contents of each patent is hereby incorporated by reference.

There is a continuing need to develop and provide clinical chemistry equipment which is not only accurate, but versatile enough to meet the demands of modern medicine. The equipment should be simple enough to be used by not only highly-skilled laboratory technicians, but also by other healthcare personnel who may be required to conduct laboratory tests from time to time. The equipment and procedures should be versatile enough so that they can be utilized in clinical laboratories which analyze thousands of samples daily, while at the same time being adaptable to doctors' offices, home healthcare agencies and nursing homes where the number of tests being conducted is not as great. In addition, the equipment should be versatile enough to be useful in conducting a wide variety of electrochemical analyses which are presently being routinely utilized. The equipment should also be adaptable to conducting electrochemical analyses for blood or other bodily fluids which will be developed in the future.

SUMMARY OF THE INVENTION

In accordance with the present invention, an analytical cartridge is provided which can be used in a centrifuge-based system for conducting electrochemical analysis of a wide variety of fluids including biological fluids. The analytical cartridge is especially adapted for analyzing fluids, such as blood or urine. The cartridge includes an electrochemical device that is adapted to be used in a wide variety of clinical tests which measure electrochemical properties of fluids.

The analytical cartridge in accordance with the present invention is composed of a housing which includes a cartridge body having a top surface, bottom surface and outer walls defining a housing perimeter. The cartridge body further includes an inner end and an outer end. Within the housing body is located a deposition well which is designed to receive fluids, such as blood and other bodily fluids, which may contain liquid and solid components. The cartridge also includes an electrochemical device for measuring the ionic activity of the fluid. The electrochemical device includes a sample inlet for receiving the fluid from the deposition well and a reference inlet for receiving a reference fluid. The electrochemical device is located more towards the cartridge body inner end than the outlet from the deposition well. This orientation of the electrochemical device prevents fluid from entering the device during centrifuging of the cartridge.

A reference fluid which is utilized during electrochemical measurements is located in a reference fluid well. The sample fluid and reference fluid are passed through passageways from their respective wells to the electrochemical device. In accordance with the present invention, transport of the reference fluid and sample fluid to the electrochemical device is achieved by pressurizing the deposition well and the reference fluid well.

The analytical cartridge may include an overflow well located in the cartridge body. The overflow well includes an inlet and an outlet wherein the overflow well is located at a position which is more towards the outer end of the cartridge than the deposition well or the sample inlet of the electrochemical device. In addition, the sample passageway includes a first passageway which connects the deposition well outlet to the overflow well inlet and a second passageway which connects the deposition well outlet to the sample inlet of the electrochemical device. The first and second passageways are integral with each other at the deposition well outlet.

During initial centrifuging, sample fluid passes from the deposition well into the sample passageway wherein the overflow well and connecting passageways provide for transfer of an accurate and reproducible amount of fluid into the sample passageway. Once centrifuging is complete, the deposition well is pressurized to provide transfer of the aliquot of sample fluid in the sample passageway to the electrochemical device. At the same time, the reference fluid well is also pressurized to provide transfer of reference fluid into the electrochemical device.

The analytical cartridge in accordance with the present invention is well-suited for use in a wide variety of clinical settings. Numerous different electrochemical analyses may be carried out by utilizing different ion-selective electrode combinations. This allows the healthcare personnel to conduct a wide variety of different electrochemical analyses on a given sample by selecting appropriate cartridges having electrochemical devices capable of measuring desired ionic properties of numerous different fluids.

The above described and many other features and attendant advantages of the present invention will become better understood by reference to the following detailed description when taken in conjunction with the accompanying drawings.

BRIEF DESCRIPTION OF THE DRAWINGS

FIG. 9 also shows a portion of the passageway leading from the reference fluid well to the electrochemical device.

DETAILED DESCRIPTION OF THE INVENTION

Figure 1:
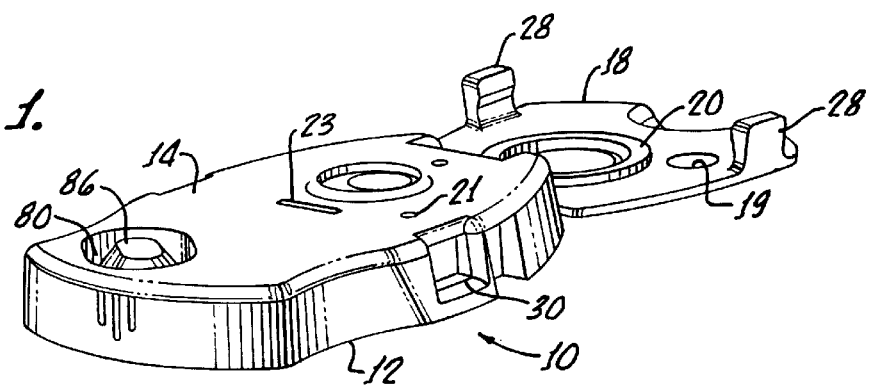
FIG. 1 is a perspective view of a preferred exemplary analytical cartridge in accordance with the present invention showing the cap which contains the flexible septum for pressurizing the deposition well in an open position.

A preferred exemplary analytical cartridge in accordance with the present invention is shown generally at 10 in FIGS. 1–3 and 8. The cartridge 10 is made up of a housing which includes a cartridge body 12, top plate 14 and label 16. The analytical cartridge 10 further includes a hinged cap 18, flexible septum 20, electrochemical device 22, and retainer plate 24. The electrochemical device 22 and retainer plate 24 are shown only in FIG. 8.

Figure 2:
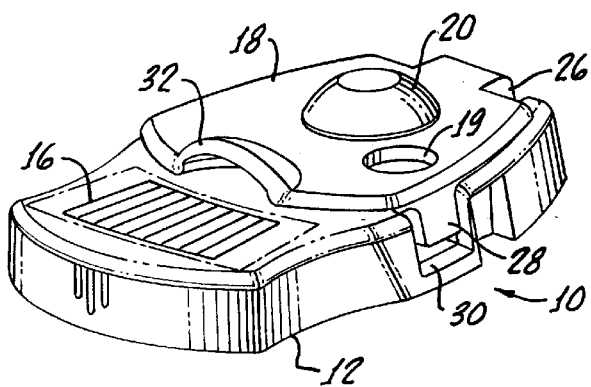
FIG. 2 is the same perspective view of the cartridge shown in FIG. 1 showing the lid in a closed position.

In FIG. 1, the analytical cartridge 10 is shown with the hinged cap 18 in the open position. In FIG. 2, the hinged cap 18 is shown in the closed position. As shown best in FIGS. 2 and 3, the cap 18 is preferably hinged to the cartridge body 12 as shown at 26. The cap 18 includes locking tabs 28 which are designed to releasably engage indentations 30 in the cartridge body 12. The cap 18 preferably includes a curved portion 32 which provides access under the cap 18 so that it can be easily opened and closed. The cap 18 and top plate 14 have vent holes 19 and 21, respectively. The cartridge body 12 and top plate 14 are preferably made from a suitable plastic, such as polystyrene, polyvinylchloride, polycarbonate, or any other plastic which is rigid and inert with respect to biological fluids. Hinged cap 18 is preferably made from a suitable plastic, such as polypropylene or polyethylene or other plastic which is flexible and inert with respect to biological fluids.

Figure 3:
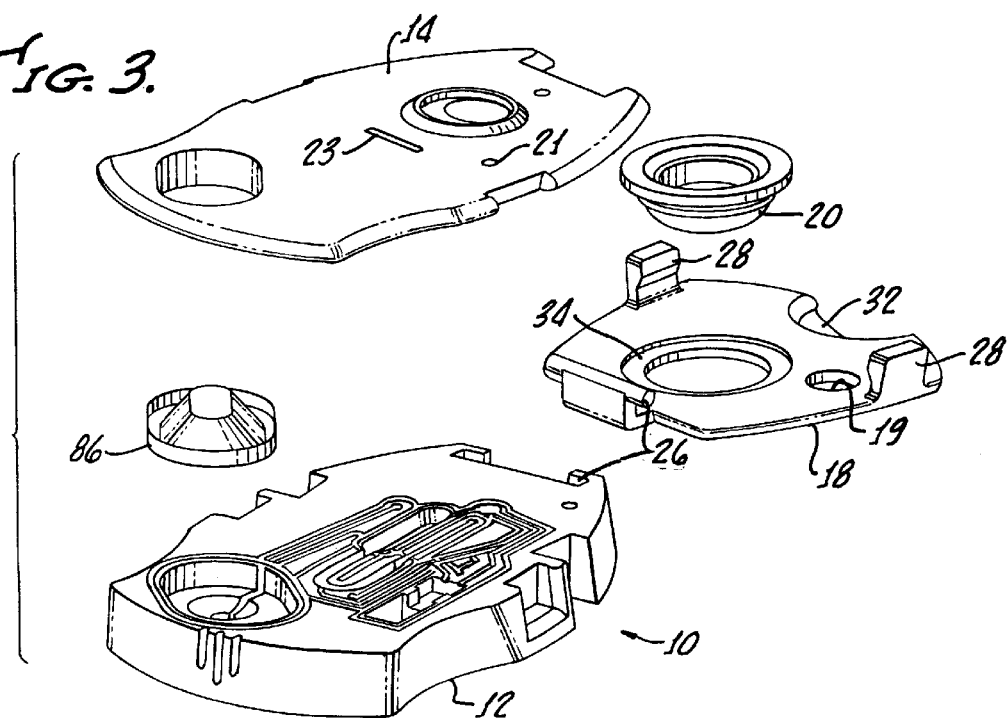
FIG. 3 is an exploded view of the preferred exemplary analytical cartridge in accordance with the present invention.

The septum 20 is shaped to fit within opening 34 in the cap 18 (FIG. 3). The septum 20 must be shaped to provide a sealing engagement with the cap 18 and top plate 14 so that depression of the septum 20 when the cap 18 is closed onto the top plate 14 results in pressure being applied to the cartridge body as will be described in more detail below. The septum 20 is made from an elastomeric material such as silicone rubber or any other elastomeric material that is inert with respect to biological fluids. The label 16 is optional and may be made from any of the well-known label materials conventionally used to allow writing onto laboratory equipment. Preferably, the label will be of the self-adhesive variety. The label 16 will preferably include an identification of the cartridge test chemistry along with instructions or other notes, such as a bar code, relevant to the specific test protocol.

Figure 4:
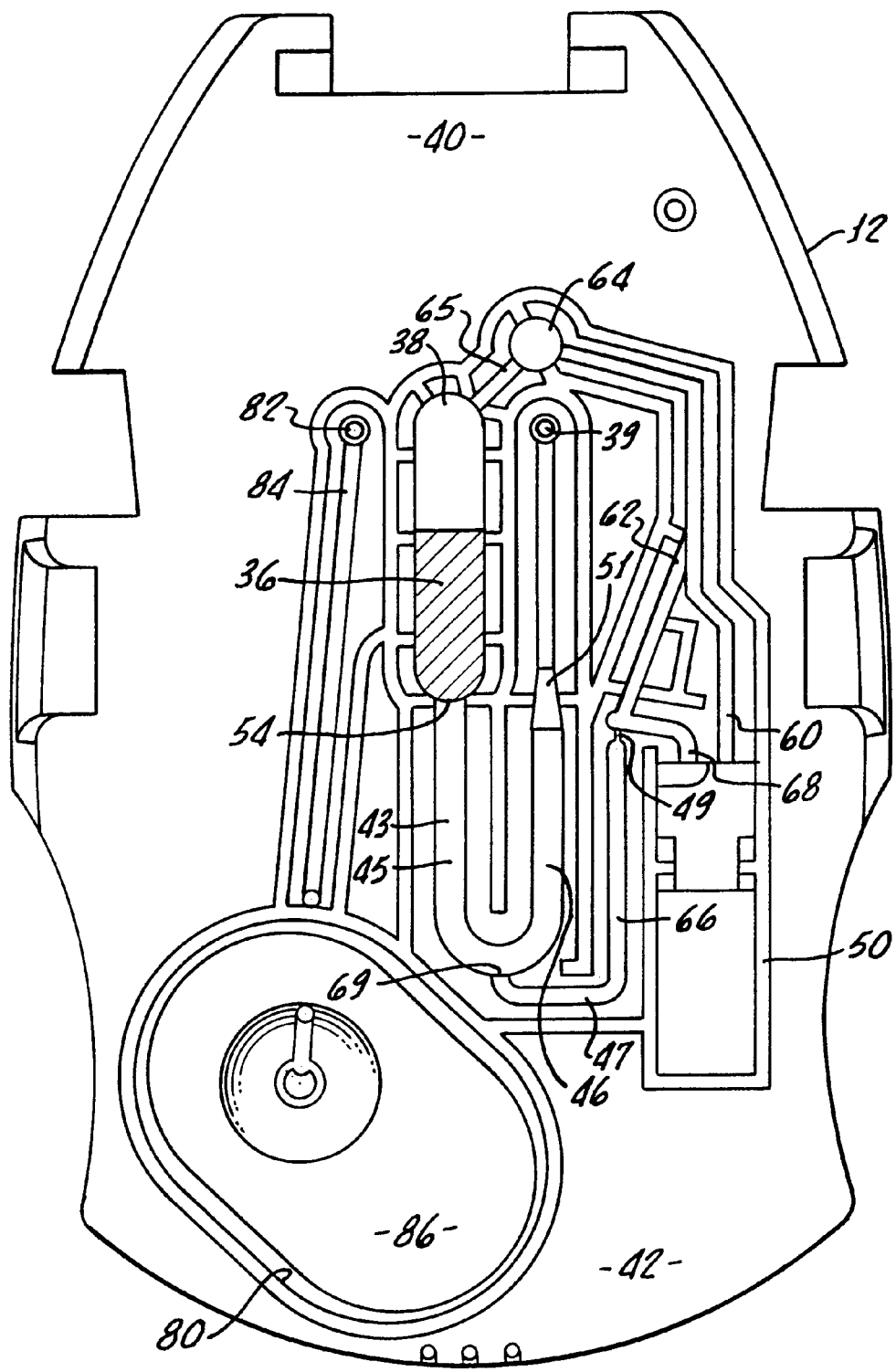
FIG. 4 is a top view of the cartridge body depicting the first step of a preferred analytical procedure wherein a fluid sample has been introduced into the deposition well.

FIGS. 4–7 are top views of the cartridge body 12 showing a preferred exemplary test cartridge at various states during the testing procedure. Referring to FIG. 4, the test cartridge 12 is shown during the first step of the analytical process where blood or other fluid sample 36 is located in deposition well 38. The cartridge body 12, as shown in FIG. 4, has an inner end 40 and an outer end 42. After the blood sample 36 has been deposited in deposition well 38, the cartridge cap 18 is closed and the cartridge is placed in a centrifuge or other apparatus which is capable of causing the blood sample 36 to be transferred towards the outer end 42 and into the sample passageway 43. Preferably, the centrifuge apparatus will be designed to house multiple cartridges which can be centrifuged simultaneously.

The top plate 14 includes a window 23 which provides visual access to the deposition well 38. The window 23 may be clear or opaque. If opaque, the window 23 must be sufficiently transparent to allow one to visually assess the contents of the deposition well 38. The window 23 is preferably in the shape of a narrow strip as shown in FIGS. 1 and 3. The window strip 23 is positioned so that blood or other sample only becomes visible when the required amount of sample has been deposited into the well 38. The window 23 allows the operator to quickly and accurately verify that the appropriate amount of sample has been deposited. Other types of detection systems may be used to verify filling of the deposition well. However, the use of a window, such as the window strip 23, is preferred due to its simplicity.

Figure 5:
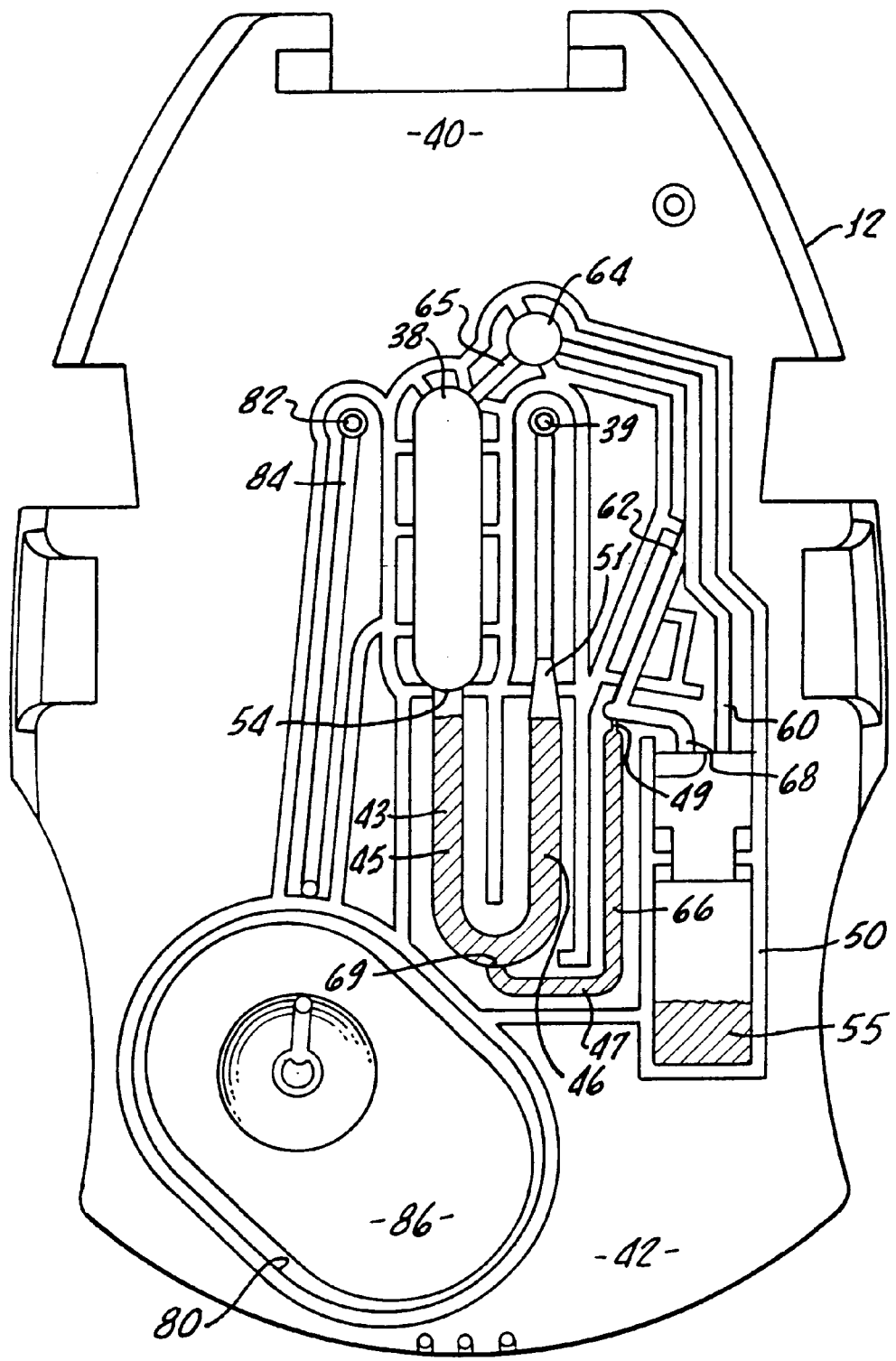
FIG. 5 depicts the cartridge body after it has been subjected to centrifugation in order to transfer an accurate amount of fluid into the sample passageway.

As shown in FIG. 5 sufficient centrifugal force is applied to the cartridge 10 to ensure that the blood, as shown at 46, is transferred into sample passageway 43. The relative sizes of the deposition well 38 and sample passageway 43 are chosen so that an excess of sample is deposited into the deposition well 38. An overflow well 50 is provided to receive the excess fluid which is transferred out of the deposition well 38 during centrifuging. The excess fluid in overflow well 50 is shown at 55.

As shown in FIGS. 4–7, the deposition well 38 is connected to the inlet 39 into the electrochemical device 22 by sample passageway 43. The sample passageway 43 performs two functions and can be thought of as a first and second passageway. The first passageway connects the sample well to the overflow well 50. A second integral passageway connects the deposition well 38 to the sample inlet 39 of the electrochemical device 22. Both the first and second passageways are integral with each other in the inlet portion of the sample passageway shown at 45. The first passageway departs from the sample passageway as shown at 47 to transport fluid to the overflow well 50 through a capillary break 49. The second passageway includes that portion of the sample passageway as shown at 51. As can be seen in FIG. 5, the location of capillary break 49 determines the amount of sample fluid which remains in the second passageway 51 after centrifuging of the cartridge. This particular orientation wherein the first passageway to the overflow well 50 and second passageway to the electrochemical device 22 are integral with each other exiting the test well 38 produces accurate and reproducible aliquots of sample in the first passageway 51.

For most electrochemical measurements, it is not necessary to separate the solid components from the fluid prior to introduction into the electrochemical device 22. However, in those situations where it is desirable to remove solids from the sample fluid prior to introduction into the electrochemical device 22, it is preferred that a separation well be included as part of the sample passageway 43. The use of separation wells in cartridges of the type disclosed herein are set forth in PCT application Nos. US98/15616 and US99/01707.

Vent passageways 60 and 62 are connected to vent opening 21 in top plate 14 to allow liquids to be transferred through the various passageways to the various wells without the build-up of back pressure. Vent passageway 62 is connected to the deposition well 38 by way of a capillary break zone 64 and vent leg 65. The capillary break zone 64 is designed to prevent inadvertent capillary flow of fluid from the deposition well 38 through passageway 62. The particular shape of capillary break zone 64 is not critical provided that there is sufficient increase in relative opening size between capillary break zone 64 and the vent leg 65 to prevent capillary action from transporting fluid from the vent leg 65 to the vent passageway 62.

As previously mentioned, the inlet portion of the sample passageway 45 in combination with the overflow passageway 47 make up the first passageway which connects the deposition well 38 to the overflow well 50. The inlet portion of the sample passageway 45, in combination with the passageway 51 forms a second passageway which connects the deposition well 38 to the electrochemical device inlet 39. As can be seen from FIGS. 4–7, the first and second passageways are integral with each at the deposition well outlet 54. The two passageways remain integral with each other until they separate at point 69.

As shown in FIG. 5, centrifuging of the analytical cartridge 10 results in the transfer of an aliquot of sample fluid into the second passageway 45 and 51. The force at which the cartridge 10 is centrifuged, as well as the time, may be varied depending upon a number of different criteria. For example, in most situations it is neither necessary nor desirable to separate cells or other components from the sample fluid. In these cases, the centrifuge time and/or force are kept at sufficiently low levels to provide flow of fluid into the passageways and overflow well 50, as described above, without separating the solid components from the fluid. The result is an accurately metered substantially homogeneous sample.

The optimum centrifuge force and time of centrifuging can be determined by routine experimentation as is well known in the art. The centrifuge load should be on the order of 200 to 400 g's with centrifuge times ranging from about 1 to 10 minutes and a time to speed of less than 3 or 4 seconds. When cell separation and removal is desired, the centrifuge parameters are chosen so that substantially all of the cellular components of the blood are separated out in a separation well (not shown). In the majority of situations where the sample is to be metered only and not separated, it is preferred to keep the centrifuge load relatively high. Separation is prevented from occurring by substantially reducing the centrifuge time periods on the order of one minute or less.

Referring again to FIG. 5, the amount of fluid which remains in the sample passageway 43 is determined by the sizes of sample passageway 43 and the configuration of overflow passageway 47. The overflow passageway 47 is preferably composed of an upstream segment 66 and an overflow well segment 68. The upstream segment 66 includes a first end that is connected to the sample passageway 43 and a second end which is connected to the overflow well segment 68. The overflow well segment 68 has a first end which is connected to the upstream segment 66 and a second end which is connected to the overflow well 50. The upstream segment 66 forms an upstream passageway in the overflow passageway 47 which has a restriction or capillary break 49 at its downstream or second end. The restriction 49 has a cross-sectional area which is substantially smaller than the cross-sectional area of the downstream passageway or overflow well segment 68 at its first end which is connected to the upstream segment 66. This reduction in cross-sectional area is required to ensure that capillary action does not adversely affect the metering process and aliquotting of liquid in the sample passageway 43. This configuration is preferred in order to provide a break in possible unwanted capillary action within the various passageways and wells. It is also preferred that the connection between the upstream segment 66 and overflow well segment 68 be offset so that the restricted opening is not in the center of either passageway. Other configurations are possible provided that relative changes in cross-sectional areas and the orientation of the connection point between the upstream and downstream portions of the overflow passageway 47 are such that capillary induced flow is prevented.

Preferably, the reduction in cross-sectional area shown in constriction 49 in FIGS. 4–7 will occur adjacent to the connection with the overflow well segment 68. Preferably, the upstream segment 66 will be a channel having widths of between 0.7 and 1.1 mm and depths of between 0.1 and 0.2 mm. The constriction 49 will have widths on the order of 0.3 to 0.5 mm and depths on the order of 0.1 to 0.2 mm. The overflow well segment 68 and the remainder of the various passageways are preferably channels also having the above widths, but depths on the order of 0.5 and 1.5 mm. It is particularly preferred that the channel dimensions for the sample passageway 43 be on the order of 1.5 mm wide by 1.5 mm deep. It is particularly preferred that the overflow passageway 47 and the ventline 60 and 62 all be on the order of 0.8 mm wide by 1.1 mm deep. The preferred dimensions for the constriction 49 is 0.4 mm wide by 0.1 mm deep. Passageways having cross-sectional configurations other than square or rectangular channels are possible.

Figure 6:
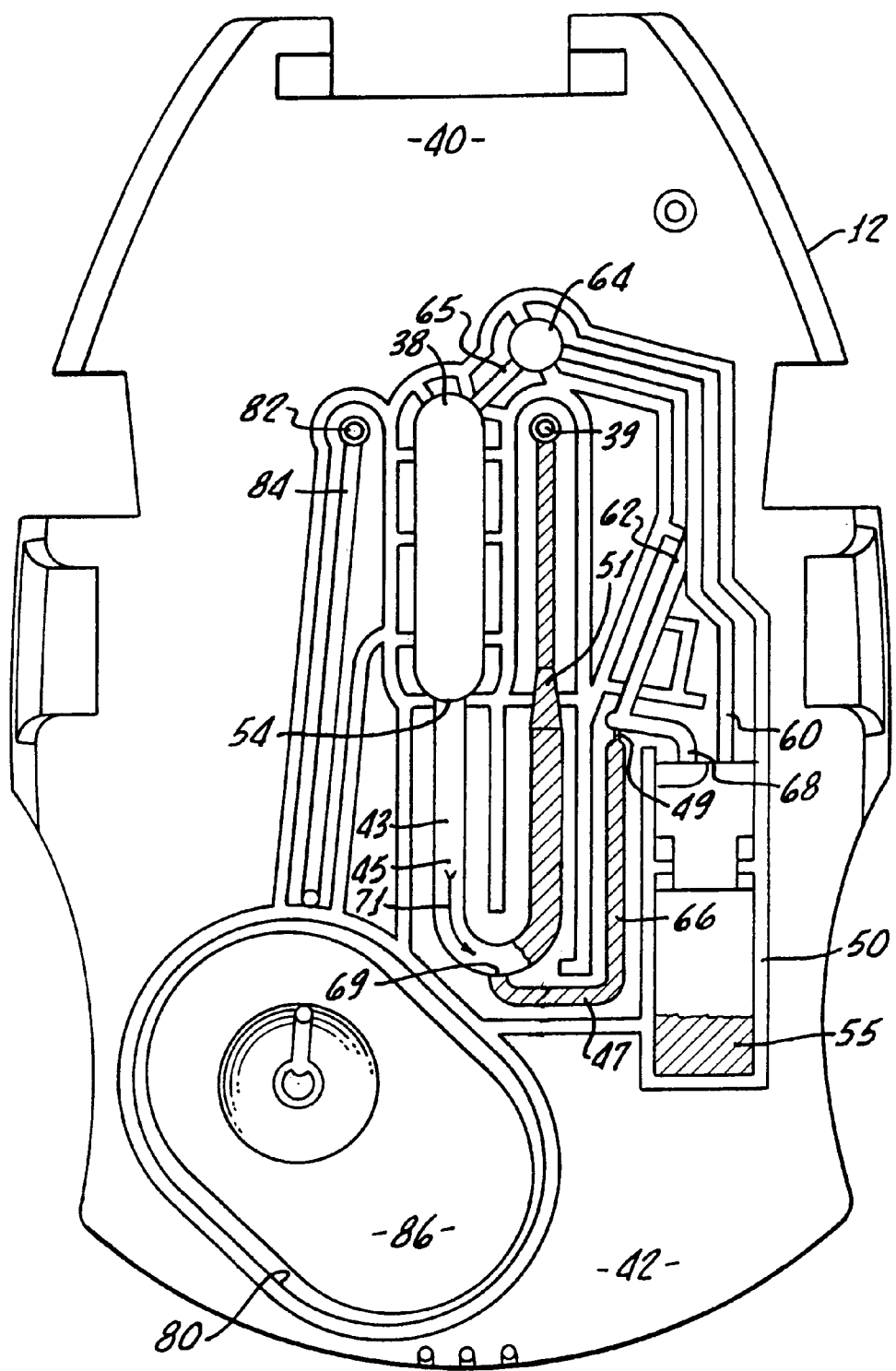
FIG. 6 is a view of the cartridge body depicting the transfer of sample fluid to the electrochemical device as a result of pressurization of the deposition well.

After completion of the centrifuging step, the sample aliquot located in the sample passageway 43 (i.e., inlet passageway 45 and passageway 51). is transported through the passageway 51 as represented by arrow 71 in FIG. 6. The liquid as shown at 72 is forced towards the electrochemical device inlet by pressure which is applied to deposition well 38 by compressing septum 20. Although it is possible to move liquid 72 into the electrochemical device 22 by pressing septum 20 by hand, it is preferred that an automatic system be utilized wherein multiple cartridges 10 are centrifuged simultaneously and then an apparatus be provided which automatically presses down on septum 20 to provide desired pressurization of deposition well 38 to force the liquid 72 into electrochemical device 22 via inlet 39. The vent 21 in the cover 14 must be sealed when the system is pressurized using septum 20.

The inlet 39 provides an inlet into the electrochemical device 22 which is held in place by retainer 24 or otherwise bonded into the cartridge body when the electrochemical device is bonded into the housing, the retainer 24 may be deleted. Although other components may form part of the electrochemical device, it is preferred that the device be made up of thick film ion specific electrodes which are arranged in the manner set forth in U.S. Pat. Nos. 4,437,970; 4,865,698; 4,528,085; 4,510,035; 4,655,899; 5,626,740; 4,555,274; 4,571,293; 4,615,788; 4,684,445; 4,871,441; and 5,021,140.

Electrochemical devices 22 which are used in accordance with the present invention typically include at least one pair of ion-selective solid electrodes wherein the electrodes for each pair are located on opposite sides of the device. Further, the devices include two liquid distribution porous members which are disposed over all of the electrodes on each side of the device. A porous capillary bridge is disposed on or between the liquid distribution porous members. This type of device is well-suited for use in cartridges in accordance with the present invention since the use of plurality of ion-selective solid electrode pairs allows one to simultaneously determine ionic activities of a plurality of different ions in a single sample aliquot. Preferred electrochemical devices are available from Fuji Photo Film Company (Kanagawa, Japan), as Fuji Photo Film Company, Ltd. is the assignee of all of the above-referenced patents.

Although any number of ionic activities can be measured, the preferred electrochemical device is one which includes three ion-selective electrode pairs which are capable of measuring sodium, potassium, and chloride ion concentrations in blood or other bodily fluid. Other exemplary ions which can be measured include calcium, carbonate, and any of the other biologically important ions which are capable of being measured using ion-selective electrodes.

Figure 7:
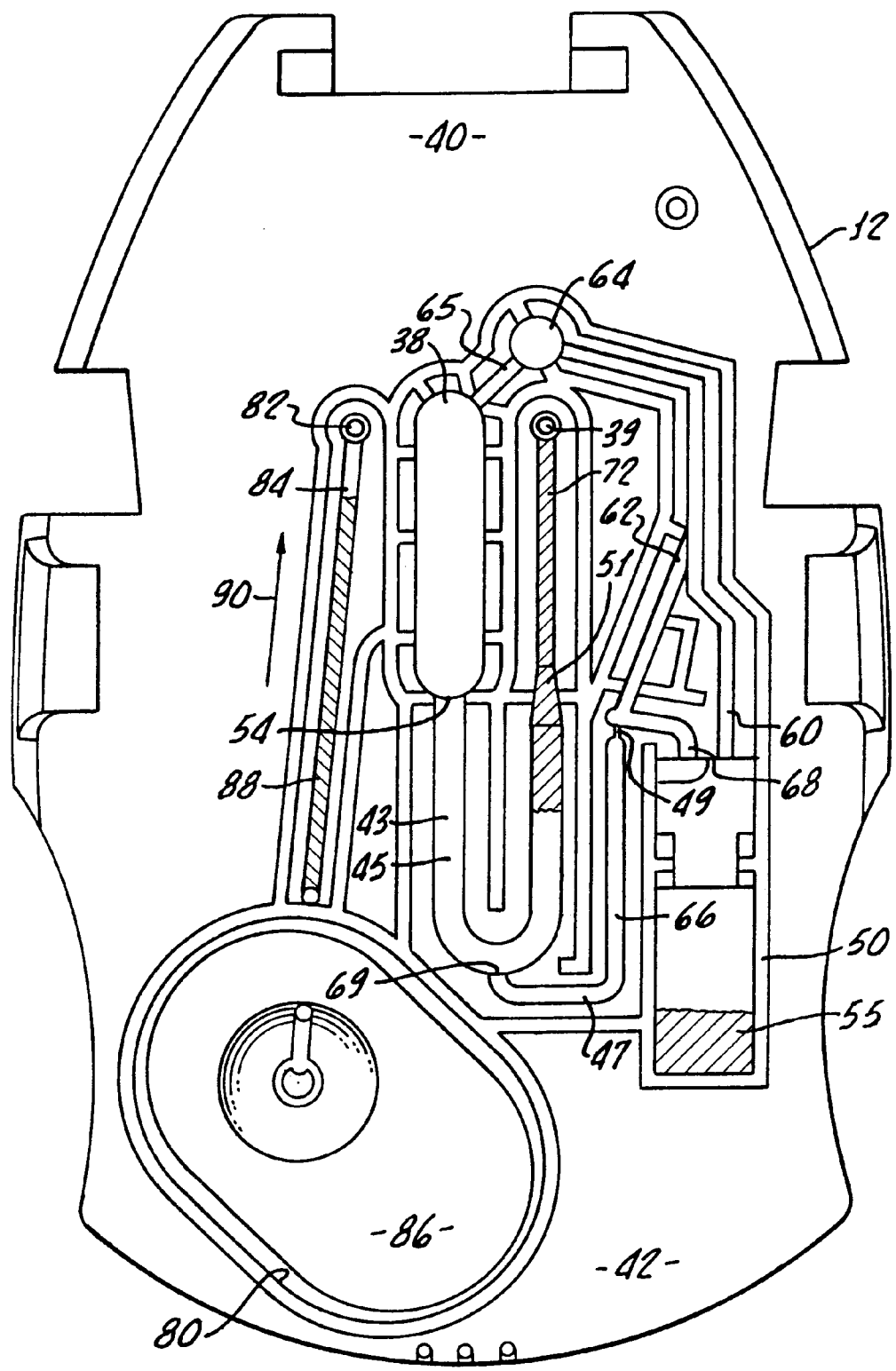
FIG. 7 is a view of the cartridge body depicting the transfer of reference fluid from the reference fluid well to the electrochemical device.
Figure 8:
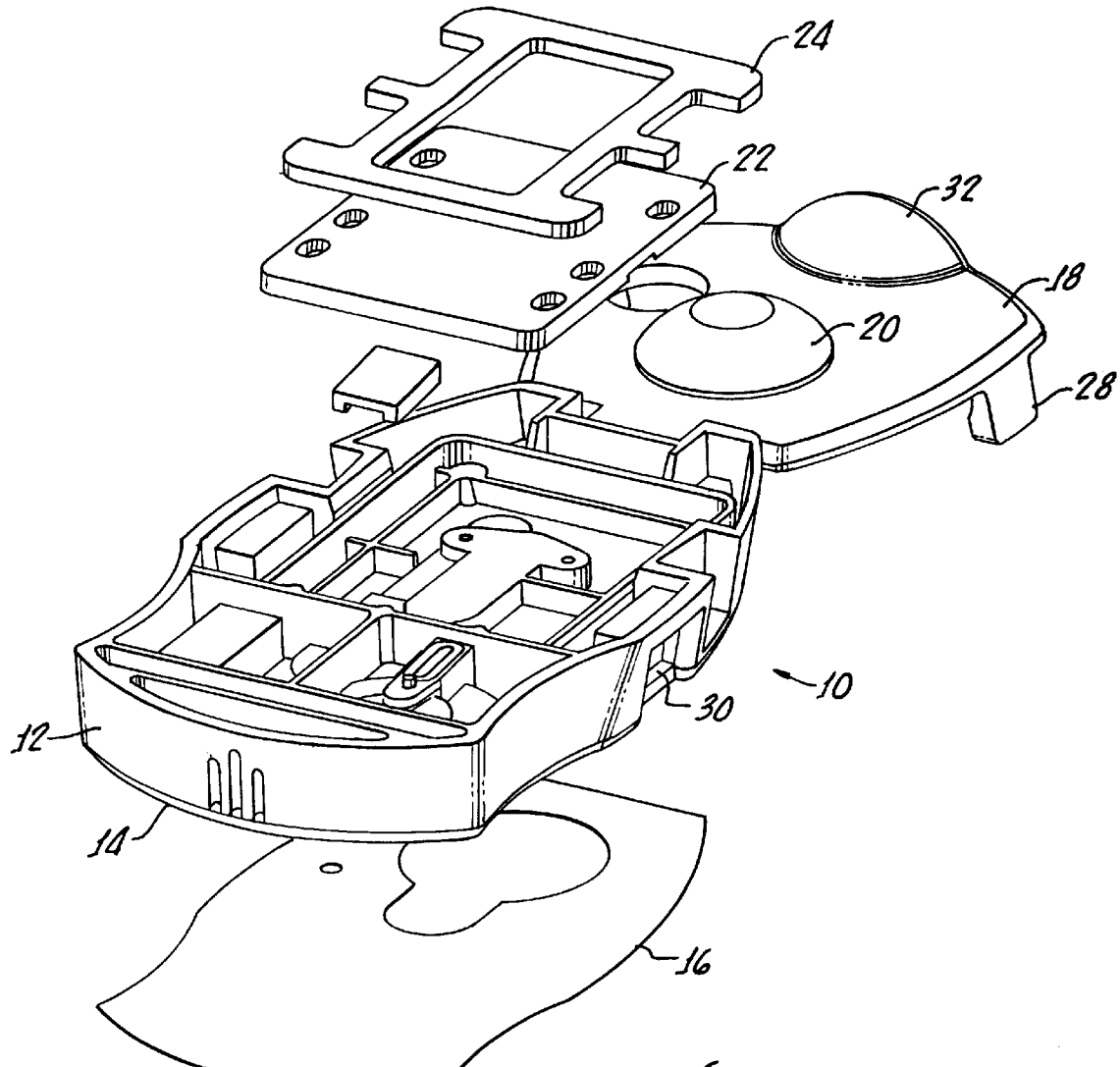
FIG. 8 is an exploded perspective view of the preferred analytical cartridge showing the electrochemical device displaced away from its location within the cartridge body.
Figure 9:
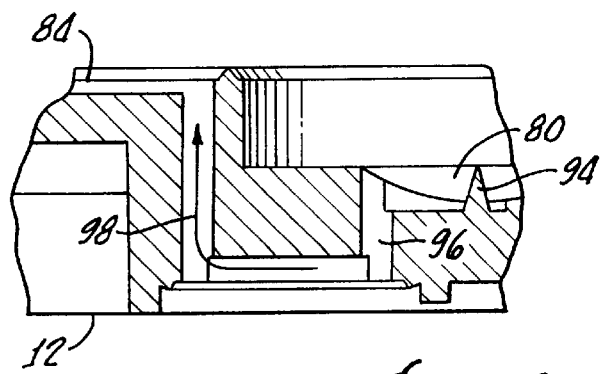
FIG. 9 is a detailed view of a portion of the reference liquid well in accordance with the present invention.

As is well known when using electrochemical devices 22 of the type set forth in the above-identified patents, it is necessary to introduce a reference fluid into the electrochemical device in order to accurately determine the ionic activity of a given sample. In the preferred embodiment of the present invention, a reference fluid well or pouch is located in the cartridge as shown in 80 in FIGS. 1, 3–7 and 9. The reference fluid well 80 is connected to the inlet 82 into electrochemical device 22 by way of passageway 84. A flexible pouch 86 (see FIGS. 1 and 3) which contains the reference fluid is placed in the reference fluid well 80. As shown in FIG. 7, application of pressure to the flexible pouch 86 results in reference fluid, as shown at 88 being transported to the electrochemical device inlet 82, as represented by arrow 90. Referring to FIG. 9, it is preferred that the bottom of the reference fluid pouch 86 be pierced by spike 94 when the pouch 86 is depressed. Upon puncture of pouch 86 by spike 94, the reference fluid flows into channel 96 and then into reference fluid passage 84 as represented by arrow 98. Other types of valving systems are possible. However, the use of a foil or other material which can be punctured by spike 94 is preferred due to its simplicity. As was the case with flexible septum 20, it is preferred that the pouch 86 be automatically depressed or squeezed by a mechanical arm or other device at an appropriate time during the analysis protocol.

The cartridge assembly, as described above, is well-suited for conducting a number of different electrochemical analyses. A wide variety of fluids, including serum, plasma, whole blood, saliva, spinal fluid, urine or other aqueous solutions may be tested. A number of different systems may be connected to the electrochemical device 22 in order to provide a read-out of the ionic activities of the sample fluids. Such systems will include electrical contacts, or probes which are inserted into contact points in the electrochemical device to provide conductance measurements between the ion-selective electrode pairs.

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiments as illustrated herein, but is only limited by the following claims.

What is claimed is:

1. An analytical cartridge for use in electrochemical analysis of fluids, said cartridge comprising:
   a housing comprising a cartridge body which has a top surface, bottom surface and outer walls defining a housing perimeter, said body further comprising an inner end and outer end;
   a deposition well located in said cartridge body for receiving fluid to be analyzed, said deposition well having an inlet and an outlet;

an electrochemical device for measuring the ionic activity of said fluid, said electrochemical device comprising a sample inlet for receiving said fluid and a reference inlet for receiving a reference fluid;

a sample overflow well located in said cartridge body, said overflow well having an inlet and outlet;

a sample metering system which comprises a sample passageway which comprises a first passageway which connects the outlet of said deposition well to the overflow well inlet and a second passageway which connects the outlet of said deposition well to the sample inlet of said electrochemical device, wherein said first and second passageways are integral with each other at said deposition well outlet;

a reference fluid well for housing reference fluid, said reference fluid well having an outlet;

a reference fluid passageway which is connected between said reference fluid well outlet and the reference inlet of said electrochemical device;

a sample pressurization device for pressurizing said deposition well to provide movement of sample fluid from said sample passageway to said electrochemical device; and a reference fluid pressurization device for pressurizing said reference fluid well to provide movement of reference fluid through said reference fluid passageway.

2. An analytical cartridge according to claim 1 wherein said electrochemical device comprises at least one thick film ion specific electrode.

3. An analytical cartridge according to claim 2 wherein said electrochemical device comprises thick film ion specific electrodes for an ion selected from the group consisting of sodium, potassium, calcium, chloride and carbonate ions.

4. An analytical cartridge according to claim 3 wherein said electrochemical device comprises ion specific electrodes for sodium ion, potassium ion and chloride ion.

5. An analytical cartridge according to claim 1 wherein said sample pressurization device comprises a flexible septum which can be moved from a relaxed position to one or more compressed positions, wherein movement from said relaxed position to said one or more compressed positions provides pressurization of said deposition well.

6. An analytical cartridge according to claim 1 wherein said reference fluid pressurization device comprises a flexible septum which can be moved from a relaxed position to one or more compressed positions, wherein movement from said relaxed position to said one or more compressed positions provides pressurization of said reference fluid well.

7. An analytical cartridge according to claim 5 wherein said septum is located in a cap, said cap being movable between an open position wherein said septum is displaced away from said deposition well to allow introduction of fluid into said deposition well and a closed position wherein said septum is in a position to provide pressurization of said deposition well.

8. An analytical cartridge according to claim 1 wherein said electrochemical device is located more towards said cartridge body inner end than the outlet from said deposition well.

9. An analytical cartridge according to claim 1 wherein said overflow well is located at a position which is more toward said outer end of the cartridge body than said deposition well or the sample inlet of said electrochemical device.

10. An analytical cartridge according to claim 8 wherein said overflow well is located at a position which is more toward said outer end of the cartridge body than said deposition well or the sample inlet of said electrochemical device.

11. An analytical cartridge for use in analyzing sample fluids, said cartridge comprising:

a housing comprising a cartridge body which has a top surface, bottom surface and outer walls defining a housing perimeter, said body further comprising an inner end and outer end;

a deposition well located in said cartridge body for receiving sample fluid to be analyzed, said deposition well having an inlet and outlet;

a test well comprising a sample inlet for receiving said sample fluid and a reference inlet for receiving a reference fluid;

a sample overflow well located in said cartridge body, said overflow well comprising an inlet and outlet;

a sample metering system which comprises a sample passageway which comprises a first passageway which connects the outlet of said deposition well to the overflow well inlet and a second passageway which connects the outlet of said deposition well to the sample inlet of said test well, wherein said first and second passageways are integral with each other at said deposition well outlet;

a reference fluid well for housing reference fluid, said reference fluid well having an outlet;

a reference fluid passageway which is connected between said reference fluid well outlet and the reference inlet of said test well;

a sample pressurization device for pressurizing said deposition well to provide movement of sample fluid from said sample passageway to said test well; and a reference fluid pressurization device for pressurizing said reference fluid well to provide movement of reference fluid through said reference fluid passageway.

12. An analytical cartridge according to claim 11 wherein said test well is located more towards said cartridge body inner end than the outlet from said deposition well.

13. An analytical cartridge according to claim 11 wherein said overflow well is located at a position which is more toward said outer end of the cartridge body than said deposition well or the sample inlet of said test well.

14. An analytical cartridge according to claim 13 wherein said overflow well is located at a position which is more toward said outer end of the cartridge body than said deposition well or the sample inlet of said test well.

15. An analytical cartridge according to claim 11 wherein said sample pressurization device comprises a flexible septum which can be moved from a relaxed position to one or more compressed positions, wherein movement from said relaxed position to said one or more compressed positions provides pressurization of said deposition well.

16. An analytical cartridge according to claim 15 wherein said reference fluid pressurization device comprises a flexible septum which can be moved from a relaxed position to one or more compressed positions, wherein movement from said relaxed position to said one or more compressed positions provides pressurization of said reference fluid well.

17. An analytical cartridge according to claim 15 wherein said septum is located in a cap, said cap being movable between an open position wherein said septum is displaced away from said deposition well to allow introduction of fluid into said deposition well and a closed position wherein said septum is in a position to provide pressurization of said deposition well.

* * * * *